United States Patent
Okwudire et al.

(10) Patent No.: US 10,077,865 B2
(45) Date of Patent: Sep. 18, 2018

(54) MAGNET ASSISTED STAGE FOR VIBRATION AND HEAT REDUCTION IN WAFER SCANNING

(71) Applicant: THE REGENTS OF THE UNIVERSITY OF MICHIGAN, Ann Arbor, MI (US)

(72) Inventors: Chinedum E. Okwudire, Ann Arbor, MI (US); Deokkyun D. Yoon, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 0 days.

(21) Appl. No.: 15/315,878

(22) PCT Filed: Jun. 3, 2015

(86) PCT No.: PCT/US2015/033940
§ 371 (c)(1),
(2) Date: Dec. 2, 2016

(87) PCT Pub. No.: WO2015/187803
PCT Pub. Date: Dec. 10, 2015

(65) Prior Publication Data
US 2017/0089506 A1 Mar. 30, 2017

Related U.S. Application Data

(60) Provisional application No. 62/007,978, filed on Jun. 5, 2014.

(51) Int. Cl.
H01L 21/67 (2006.01)
F16M 11/04 (2006.01)
(Continued)

(52) U.S. Cl.
CPC ........... *F16M 11/043* (2013.01); *F16M 11/18* (2013.01); *G03F 7/709* (2013.01);
(Continued)

(58) Field of Classification Search
CPC .................................................. H01L 21/67259
(Continued)

(56) References Cited

U.S. PATENT DOCUMENTS

6,054,784 A * 4/2000 Sperling ............. G03F 7/70716
108/20
7,002,668 B2 2/2006 Rivin
(Continued)

OTHER PUBLICATIONS

International Search Report and Written Opinion issued in PCT/US2015/033940, dated Oct. 14, 2015; ISA/KR.
(Continued)

*Primary Examiner* — David S Luo
(74) *Attorney, Agent, or Firm* — Harness, Dickey & Pierce, P.L.C.

(57) ABSTRACT

A magnet assisted stage system for scanning applications having a scanning table being moveable from a first position to a second position, a scanning actuator operably associated with the scanning table to move the scanning table along a scanning direction from the first position to the second position, and an actively variable magnetic spring system being operably augmented to the scanning table to exert a magnetic repulsion force upon the scanning table in the scanning direction.

14 Claims, 11 Drawing Sheets

(51) Int. Cl.
*F16M 11/18* (2006.01)
*G03F 7/20* (2006.01)
*G01N 21/95* (2006.01)

(52) U.S. Cl.
CPC .... *H01L 21/67259* (2013.01); *G01N 21/9501* (2013.01); *G01N 2201/103* (2013.01)

(58) Field of Classification Search
USPC ...................................................... 318/3, 34
See application file for complete search history.

(56) References Cited

U.S. PATENT DOCUMENTS

| | | | |
|---|---|---|---|
| 7,006,199 B2 * | 2/2006 | Munnig Schmidt | ......................... G03F 7/70758 355/72 |
| 7,248,339 B2 | 7/2007 | Van Schothorst et al. | |
| 7,417,711 B2 * | 8/2008 | Jacobs | .................... G03F 7/709 355/53 |
| 8,144,310 B2 | 3/2012 | Butler et al. | |
| 2005/0200826 A1 | 9/2005 | Schmidt | |
| 2007/0059076 A1 | 3/2007 | Wei | |
| 2007/0062398 A1 | 3/2007 | Butler | |
| 2008/0165403 A1 | 7/2008 | Grasshoff et al. | |
| 2013/0321892 A1 | 12/2013 | Haeberle et al. | |

OTHER PUBLICATIONS

Yoon et al., "Magnet assisted stage for vibration and heat reduction in wafer scanning", CIRP Annals—Manufacturing Technology, 64 (2015), pp. 381-384.

Yoon et al., "Active assist device for simultaneous reduction of heat and vibrationin precision scanning stages", Precision Engineering, 46 (2016), pp. 193-205.

Schmidt, "Ultra-precision engineering in lithographic industry exposure equipment for the semiconductor", Philosophical Transactions of the Royal Society A, 370 (2012), pp. 3950-3972.

Brown et al., "A Maneuver Based Design of a Passive-Assist Device for Augmenting Active Joints", Journal of Mechanisms and Robotics, 5 (2013), pp. 031003-1-031003-2.

* cited by examiner

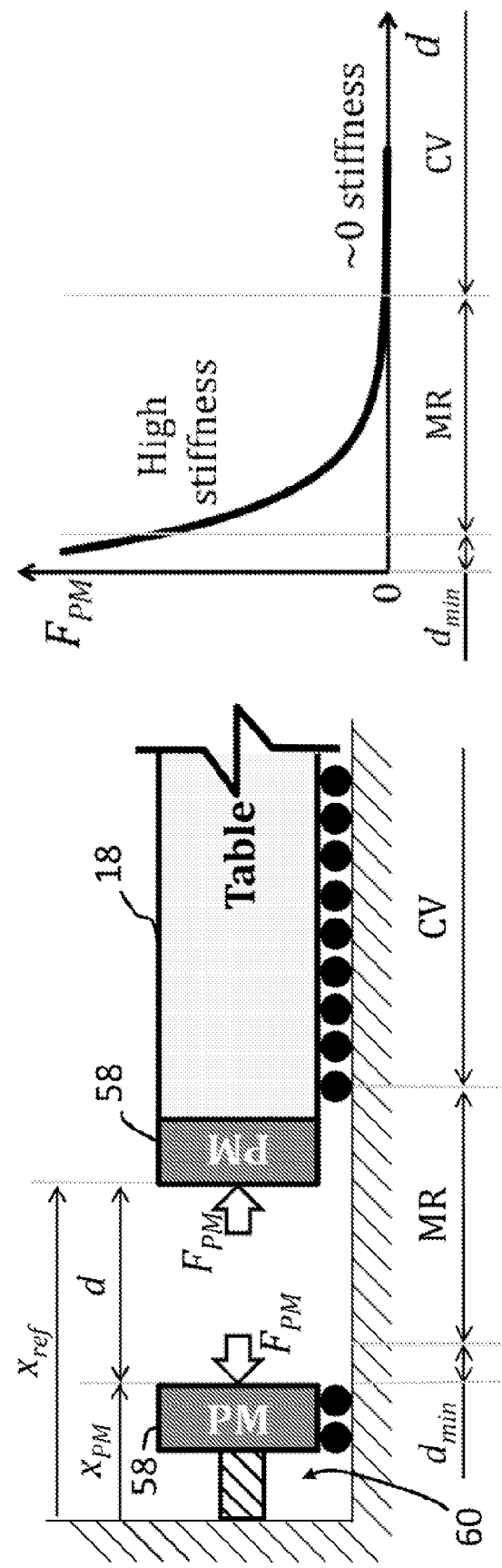

MAGNET ASSISTED STAGE FOR VIBRATION AND HEAT REDUCTION IN WAFER SCANNING

CROSS-REFERENCE TO RELATED APPLICATIONS

This application claims the benefit of U.S. Provisional Application No. 62/008,978, filed on Jun. 5, 2014. The entire disclosure of the above application is incorporated herein by reference.

GOVERNMENT INTEREST

This invention was made with government support under CMM11350202, awarded by the National Science Foundation. The Government has certain rights in the invention.

FIELD

The present disclosure relates to an active assist stage for scanning applications and, more particularly, to a magnet assisted stage for vibration and heat reduction in wafer scanning.

BACKGROUND AND SUMMARY

This section provides background information related to the present disclosure which is not necessarily prior art. This section also provides a general summary of the disclosure, and is not a comprehensive disclosure of its full scope or all of its features.

Scanning stages are used for precise positioning in a variety of advanced manufacturing processes, such as laser patterning, 3-D printing, and pick-and-place type applications for hard drive manufacturing. In particular, they are used for precise positioning at various stages of silicon wafer processing, such as optical lithography and inspection.

In response to increased throughput demands, wafer scanning stages must deliver high accelerations/decelerations (acc/dec) at motion reversals. The resulting high inertial forces that are borne by the linear motor actuators cause Joule heating proportional to the square of the motor current, leading to increased thermal errors. Various methods such as forced cooling, thermal error compensation, light-weighting and optimal control of the motor drives can be used to mitigate thermal errors. Unfortunately, forced cooling requires cooling circuits and external heat exchangers, which add to design complexities and raise costs. Effective thermal error compensation requires reliable thermal models and temperature sensor networks. Light-weighting could reduce structural stiffness and introduce unwanted vibrations. Control techniques can only offer incremental benefits for a given motor design.

In addition to generating excessive heat, the high inertial forces in scanning stages cause residual vibration of the machine frame, which adversely affects positioning speed and precision. Various methods such as tuned mass dampers, input shaping and counter motion devices can be employed to mitigate residual vibration. Tuned mass dampers and input shapers lose effectiveness when operating conditions change. Counter motion devices are bulky, expensive and energy intensive.

A passive assist device (PAD) is a spring mounted in series or parallel with an active element (e.g., motor). A passive assist device consisting of a torsional spring in parallel with a rotary motor has been illustrated to significantly reduce motor currents and power, when properly tuned for a family of motion trajectories. However, the passive assist device could increase motor currents/heat for operating conditions other than the ones for which it was tuned, making it limited in versatility.

According to the principles of the present teachings, a passive assist device is provided that uses magnetic repulsion to simultaneously reduce vibration and heat during motion reversals in wafer scanning. In some embodiments, a pair of repelling permanent magnets is used to store and release the stage's kinetic energy during deceleration and acceleration, respectively, to alleviate motor force requirements thereby reducing heat. In some embodiments, residual vibrations are lessened by channeling the assistive forces provided by the magnets to the ground, instead of to the vibration-sensitive machine base. The magnets can be automatically positioned to provide optimal assist for a given scan trajectory, thus enhancing the versatility of the passive assist device. The following discussion describes the magnet-based passive assist device in greater detail, including the design, sizing and control of a prototype magnet assisted stage. Experimental results obtained from an exemplary stage are presented and discussed.

Furthermore, in some embodiments, a magnet assisted stage system is provided for scanning applications having a scanning table being moveable from a first position to a second position, a scanning actuator operably associated with the scanning table to move the scanning table along a scanning direction from the first position to the second position, and an actively variable magnetic spring system being operably augmented to the scanning table to exert a magnetic repulsion force upon the scanning table in the scanning direction.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 2A illustrates a portion of a schematic view of a scanning stage having a passive assist device employing magnetic repulsion according to the principles of the present teachings;

FIG. 2B is a graph illustrating characteristic force vs. distance curve of a pair of repelling permanent magnets;

Corresponding reference numerals indicate corresponding parts throughout the several views of the drawings.

DETAILED DESCRIPTION

Figures 1A, 1B:
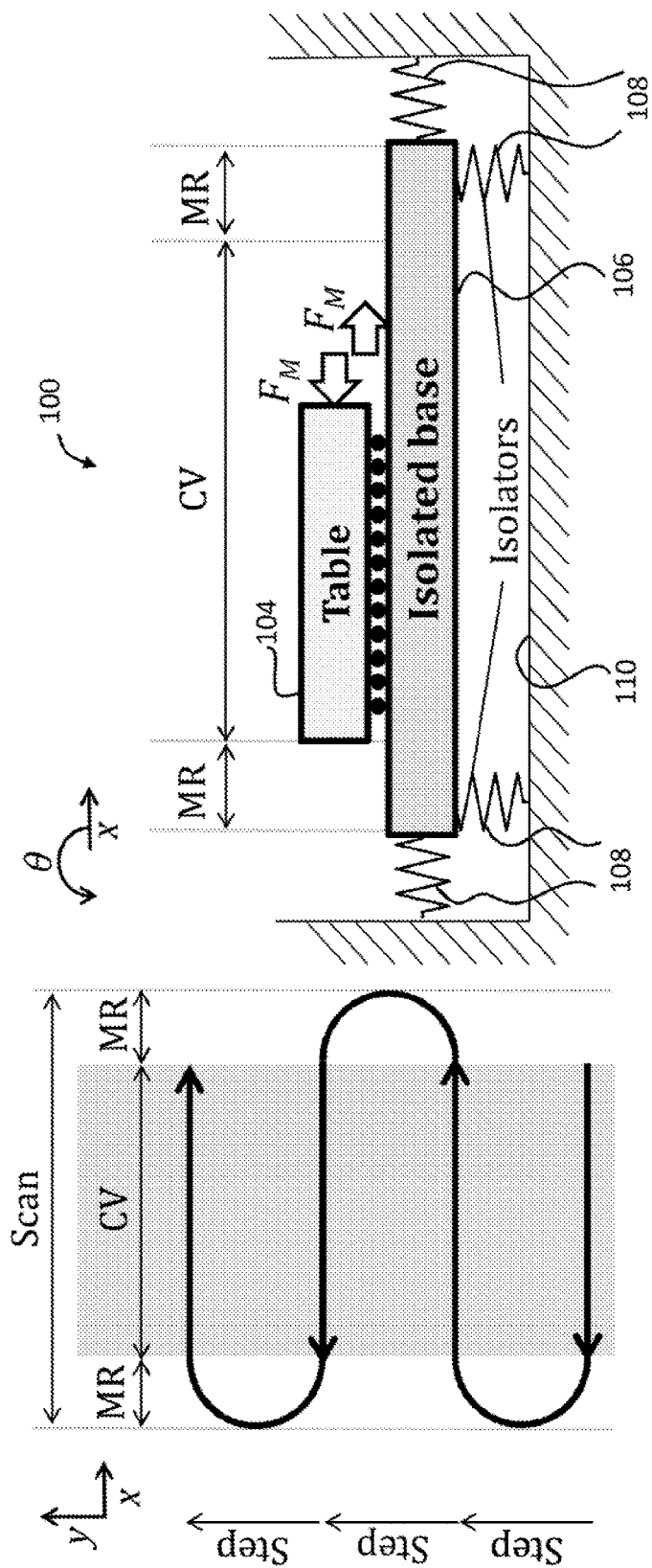
FIG. 1A illustrates regions of a silicon wafer scanning profile.
FIG. 1B illustrates a schematic view, along an x-axis, of a silicon wafer scanning stage.

Example embodiments will now be described more fully with reference to the accompanying drawings. Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Magnet Assisted Stage Device

Combined vibration and heat reduction using passive assist devices

FIG. 1A illustrates the conventional scanning profile for a silicon wafer. The y-axis advances in successive steps while the x-axis shuttles back and forth (i.e., scans) repeatedly. The scanning motion of the x-axis is the main focus of the present teachings. It consists of a constant velocity (CV) and motion reversal (motion reversal) regions. The constant velocity region of each scan is where the actual manufacturing process (e.g., lithography or inspection) takes place, so positioning must be extremely precise. The motion reversal regions are not useful to the actual manufacturing process; they must therefore be executed as fast as possible (i.e., with high acceleration/deceleration) to boost throughput while ensuring that the precision of the constant velocity regions is not compromised.

A schematic of the x-axis of a conventional wafer scanning stage 100 is illustrated in FIG. 1B. The scanning table 104, actuated by motor force $F_M$, is mounted on a rigid base 106. The base 106 is isolated from ground vibration using very soft springs 108 (conventionally pneumatic isolators) in order to achieve the desired precision in the constant velocity regions. However, when the table 104 is in the motion reversal regions, the presence of the soft springs causes unwanted horizontal and rocking (i.e., θ) vibration of the base 106 due to the large inertial forces present during acceleration/deceleration. Upon arriving at the next constant velocity region, the stage 100 must wait for the residual vibration to settle before the manufacturing process resumes, thus slowing down the process. Moreover, large inertial forces draw high electric currents from the motors, causing unwanted heat that compromises accuracy in the constant velocity regions.

Figure 1C:
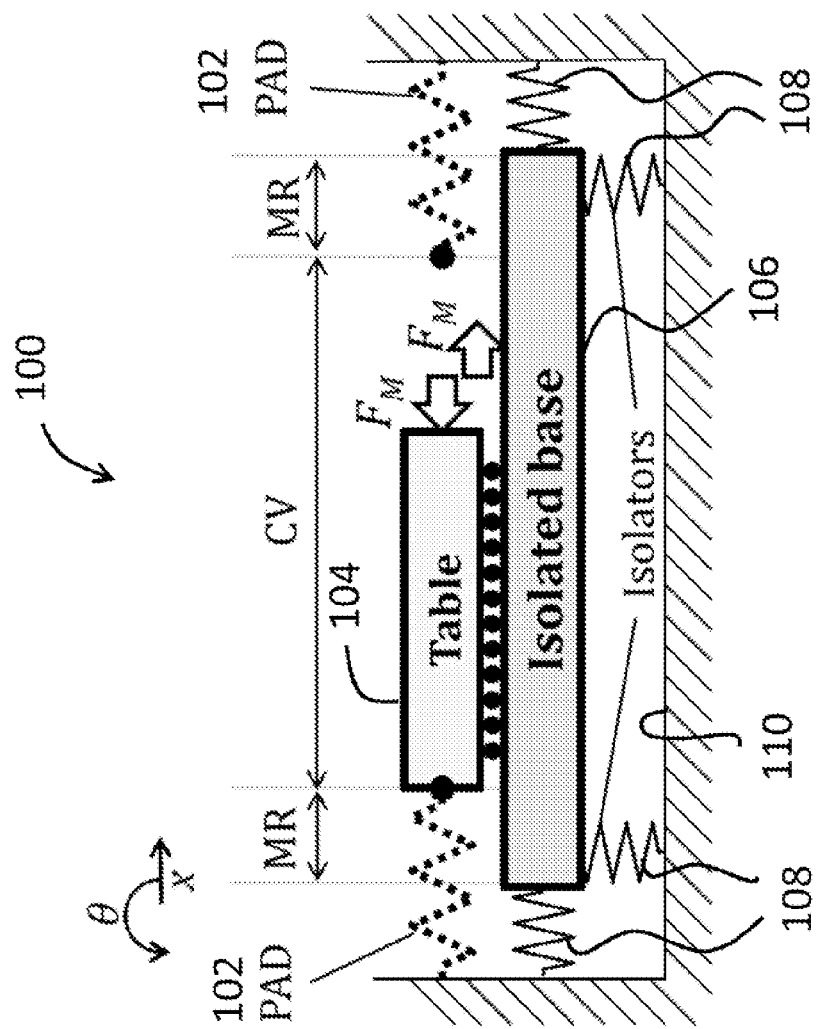
FIG. 1C illustrates a schematic view, along an x-axis, of a silicon wafer scanning stage including passive assist devices (PAD)

The present teaching provides an approach for simultaneously reducing vibration and heat using passive assist devices. As illustrated in FIG. 1C, the passive assist devices 102 are designed to store and release some of the table's kinetic energy when the table is in the motion reversal regions, thus reducing heat by lowering the magnitude of $F_M$ needed for acceleration/deceleration. Vibrations are reduced by transmitting the reaction forces from the passive assist devices 102 directly to the ground 110 so that they do not disturb the vibration-sensitive base 106 of the machine. An ideal passive assist device 102 would store and release all of the stage's kinetic energy. Additionally, it would disengage completely from the scanning table upon entering the constant velocity regions to stop the transmission of ground vibrations to the table, and to prevent the actuators ($F_M$) from doing unnecessary work against the passive assist device 102 to maintain the stage at constant velocity.

Approximation of ideal passive assist device by magnets with tunable stiffness

According to the principles of the present teachings, the ideal passive assist device 102 described herein can be substantially achieved using a pair of repelling permanent magnets (PMs); one mounted to the moving table and the other fixed just outside the motion reversal region (as illustrated in FIG. 2A). Magnetic repulsion provides a nonlinear stiffness relationship as illustrated in FIG. 2B, which is almost zero when the distance d between the magnets is large, but grows exponentially as d decreases. The effective stiffness of the device is made tunable by allowing $x_{PM}$, the position of the permanent magnets just outside the motion reversal region, to be adjustable. Therefore, an optimal $x_{PM}$ value can be determined for any desired motion profile $x_{ref}(t)$ of the stage (t denotes time). For instance, to minimize heat, $x_{PM}$ can be selected to minimize the resistive losses in the motor, represented by the objective function $f_H$ given by $$f_H = \int_0^T \left(\frac{F_M(t)}{K_M}\right)^2 dt \approx \int_0^T \left(\frac{m\ddot{x}_{ref}(t) - F_{PM}(t)}{K_M}\right)^2 dt \quad (1)$$

where $K_M$ is the motor constant and m is the moving mass of the stage. T is the time period of one scan cycle (consisting of 1 constant velocity and 2 motion reversal regions). $F_{PM}(t)$ can be calculated from the known $F_{PM}(d)$ curve of the permanent magnet pair making up a passive assist device according to the expression $$F_{PM}(t) = F_{PM}(d(t)) = F_{PM}(x_{ref}(t) - x_{PM}) \quad (2)$$

The minimization of residual vibration can be realized approximately by selecting $x_{PM}$ to minimize the peak motor force represented by the objective function $f_V$ expressed as $$f_V = \max_{t \in [0,T]} (|F_M(t)|) \approx \max_{t \in [0,T]} (|m\ddot{x}_{ref}(t) - F_{PM}(t)|) \quad (3)$$

Note that, with $x_{PM}$ determined using Eq. (1) or (3), $d_{min}$, the minimum gap between a permanent magnet pair for a given scan trajectory, can be determined as $$d_{min} = \max\left[\min_{t \in [0,T]} (|x_{ref}(t) - x_{PM}|), \delta\right] \quad (4)$$

where $\delta$ represents a safe gap between the magnets to prevent them from colliding.

Design, Sizing and Control

Design

Accordingly, a magnet assisted stage 10 is provided according to the principles of the present teachings. Although the present stage 10 will be described in connection with a specific embodiment of the present teachings, it should be understood that the principles of the present teachings can find utility in a wide variety of embodiments. By way of non-limiting example, it should be understood that the present teachings can find utility in scanning stages having different dimensions, velocities, accelerations, weights, and/or uses. Therefore, the present discussion should not be regarded as limiting the present invention and scope of the associated claims.

Figure 3:
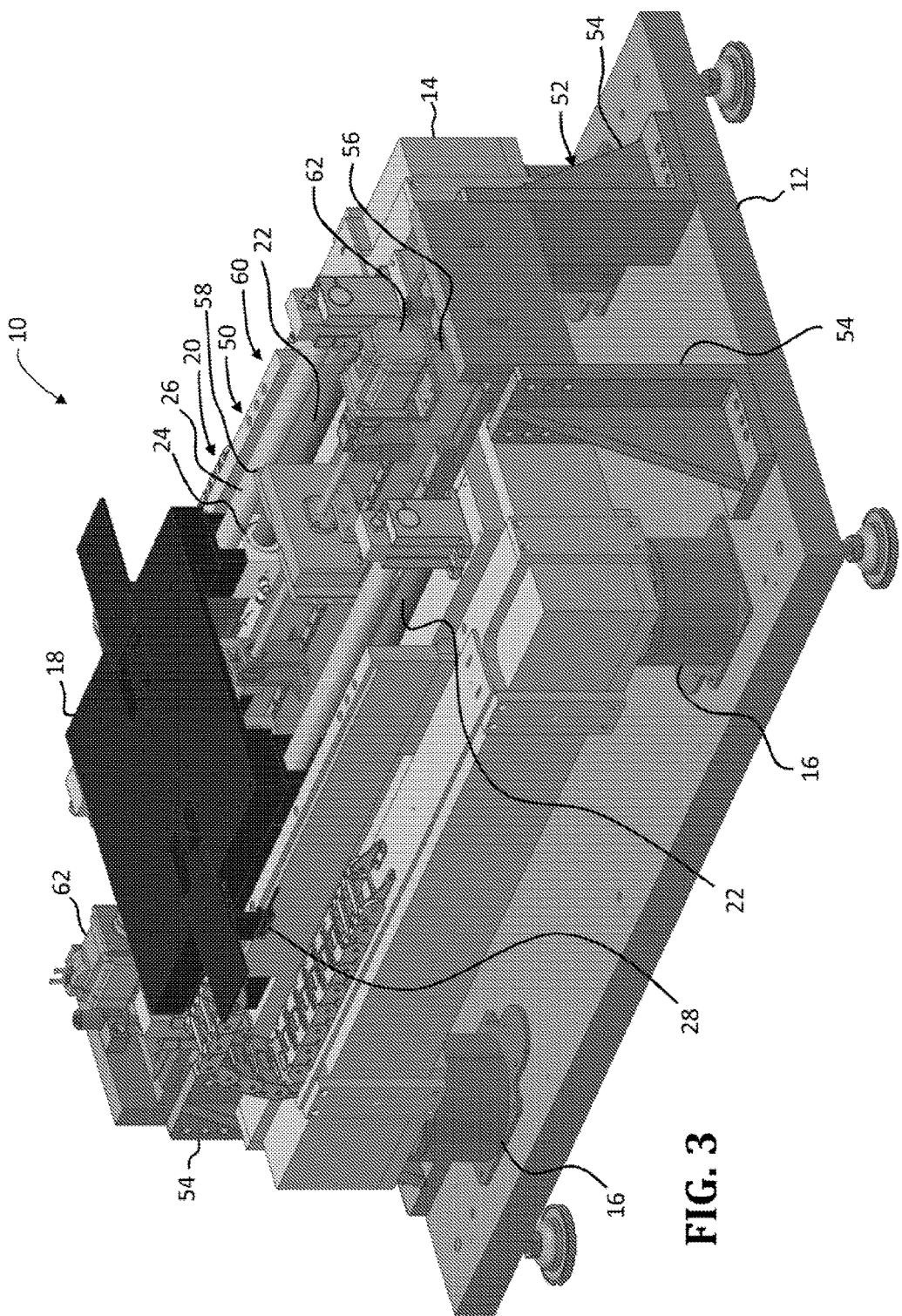
FIG. 3 illustrates a perspective view of a magnet assisted stage system according to some embodiments of the present teachings.

Therefore, by way of non-limiting example, Table 1 summarizes the design targets for the stage of the present embodiment and FIG. 3 illustrates an exemplary scanning stage 10 according to the present teachings.

TABLE 1

| Design target of magnet assisted stage prototype. | |
|---|---|
| Specification | Design target |
| Travel | 300 mm |
| Max. acceleration | 35 m/s² (3.5 g) |
| Max. scan speed | 1 m/s |
| Table size | 360 mm × 360 mm |
| Moving mass | ~15 kg |

With particular reference to FIG. 3, in some embodiments, magnet assisted stage system 10 of the present teachings can comprise a base structure 12 being coupled to or otherwise functionally equivalent to ground. An isolated base 14, such as a granite base, is operably coupled to base structure/ground 12 via a plurality of isolators 16, such as pneumatic isolators. A scanning table 18 is movably coupled relative to isolated base 14 via a support system 20. In some embodiments, support system 20 can comprise one or more guiding elements 22 being operably coupled to isolated base 14 to provide a support to permit guided movement of scanning table 18 relative to isolated base 14. Guiding elements 22 can be sized and shaped to complementarily engage a corresponding feature of scanning table 18 to provide smooth articulation. Scanning table 18 can be supported by air bushings or other reduced friction supports 24. Magnet assisted stage system 10 can further comprise a drive mechanism 26 for "scanning" movement of scanning table 18.

By way of non-limiting example, in some embodiments, scanning table 18 is guided by a set of air bushings 24 riding on a set of 25 mm precision ground shafts 22. A pair of linear shaft motors 26 with 600 N peak and 150 N continuous force (combined) is selected to drive scanning table 18. The position of scanning table 18 can be measured using linear encoders 28 with 4.88 nm resolution post-interpolation. The scanning table 18 can sit on a 900 mm×600 mm×100 mm granite base 14 suspended by four pneumatic isolators 16.

Still further, magnet assisted stage system 10 can comprise a magnetic spring system 50 for use in the stepping direction, the scanning direction, and/or the stepping and scanning directions. Magnetic spring system 50 can comprise a bridge system 52 having upright support members 54 and a support member 56 extending therebetween. Support member 56 can be disposed between isolated base 14 and scanning table 18, yet physically isolated therefrom to prevent transmission of vibration and/or heat to scanning table 18. Magnet spring system 50 can comprise one or more permanent magnets 58 installed on opposing sides of scanning stage 18 (only one illustrated; a second one is obscured by scanning table 18 in FIG. 3). The particular design, size, and configuration of permanent magnets 58 will be described herein.

In some embodiments, the position and, thus, the magnetic force exerted by permanent magnet 58 can be varied and/or adjusted by use of a magnet drive system 60 having a motor 62 operably coupled to at least one of permanent magnets 58 to vary a distance between permanent magnet 58 and scanning table 18. In some embodiments, a servo having a single linear guide and a 10 mm-diameter rolled ball screw driven by a stepper motor can be employed to automatically adjust the position of one or more permanent magnets 58 on the motion reversal side of scanning table 18. It should be noted that magnet drive system 60 can be mounted upon bridge system 52, thus allowing the assistive forces to be conducted to the ground without disturbing scanning table 18 and/or isolated base 14.

Sizing of Magnets

In some embodiments, magnet assisted stage system 10 can be compact yet provide assistive forces of at least 525 N (the maximum inertial force requirement) to scanning table 18 at the minimum gap allowed between permanent magnets 58. Therefore, in some embodiments, a 2-D Halbach arrangement, which is well-known to provide high force densities, can be employed.

Figure 4:
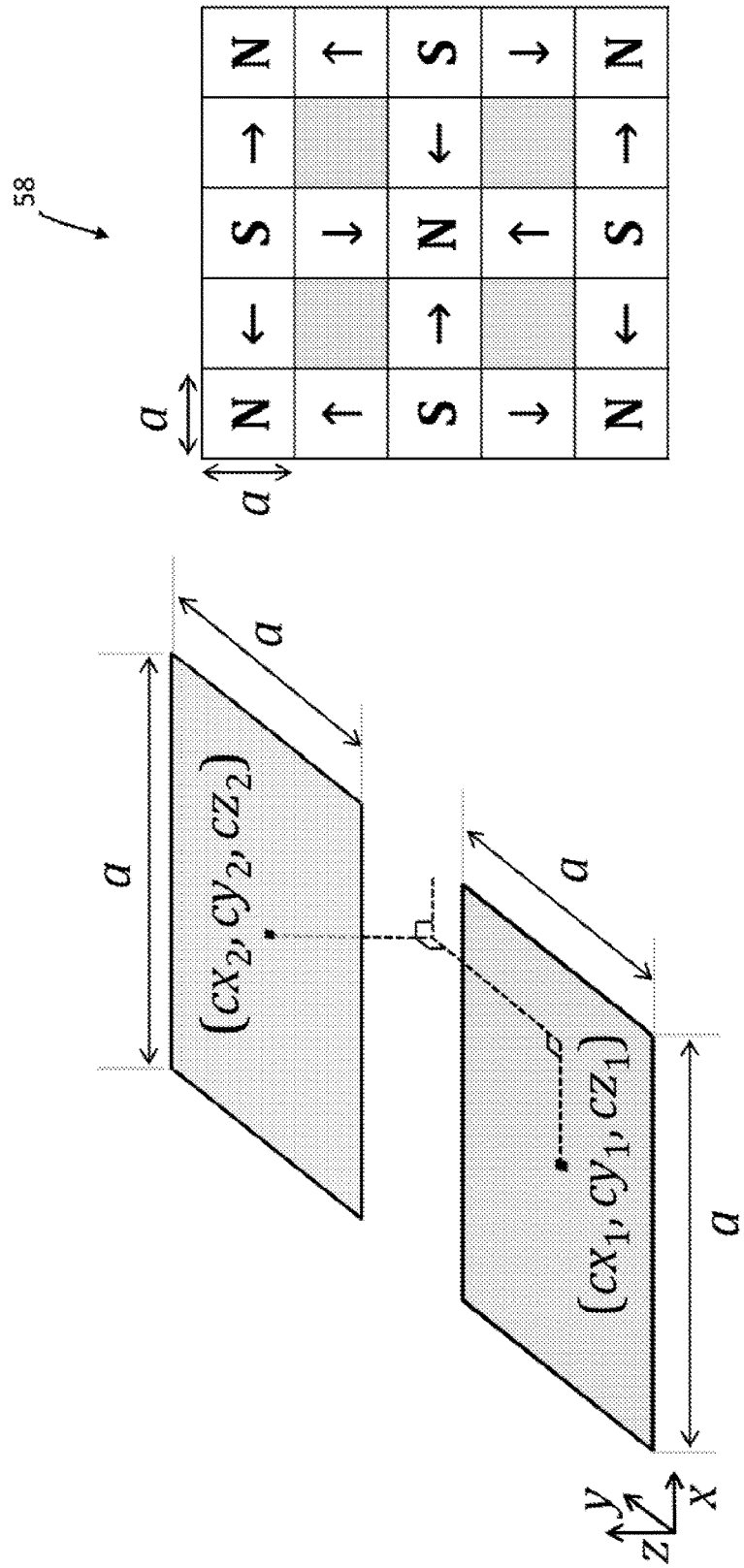
FIG. 4A illustrates a schematic view of a simplified Coulombian magnetic force model for determining force between two magnetized surfaces.
FIG. 4B illustrates a magnetic pole arrangement of 2-D Halbach array, with arrows indicating North pole direction and gray spaces indicating absence of magnets.

A simplified Coulombian model is used to estimate the magnetic force between the two Halbach arrays for sizing purposes. FIG. 4A depicts the interaction between the surfaces (of dimension a×a) of two magnets, based on the Coulombian model. $cx_i$, $cy_i$, and $cz_i$ are respectively the x, y and z coordinates of the center of each surface (i=1, 2). The equation describing the force F between the two magnetized surfaces is given by $$F = \frac{\sigma_1 \sigma_2 a^2}{4\pi\mu_0} \int_{cy_1-a/2}^{cy_1+a/2} \int_{cx_1-a/2}^{cx_1+a/2} \frac{p_{1,2}}{|p_{1,2}|^3} dx_1 dy_1 \quad (5)$$

with position vector $p_{1,2}$ expressed as $$p_{1,2} = (cx_2 - x_1)i + (cy_2 - y_1)j + (cz_2 - cz_1)k \quad (6)$$

where $\mu_0 = 4\pi \times 10^{-7}$ H/m is the permeability of free space and $\sigma$ is magnetic flux density of each surface. In some embodiments, 21 N42 grade NdFeB PM cubes with $|\sigma|=1.32$ T are used to construct each Halbach array (permanent magnet 58), as illustrated in FIG. 4B. The net force between the two arrays at a given distance can be found by summing the forces between all the magnetized surfaces of the two arrays. Permanent magnet dimension a=7.9375 mm (5/16 in.) is predicted to meet the assistive force requirements of the stage using two identical Halbach arrays for each permanent magnet (i.e., there are a total of four arrays for each passive assist device).

Controller Design

Figure 5:
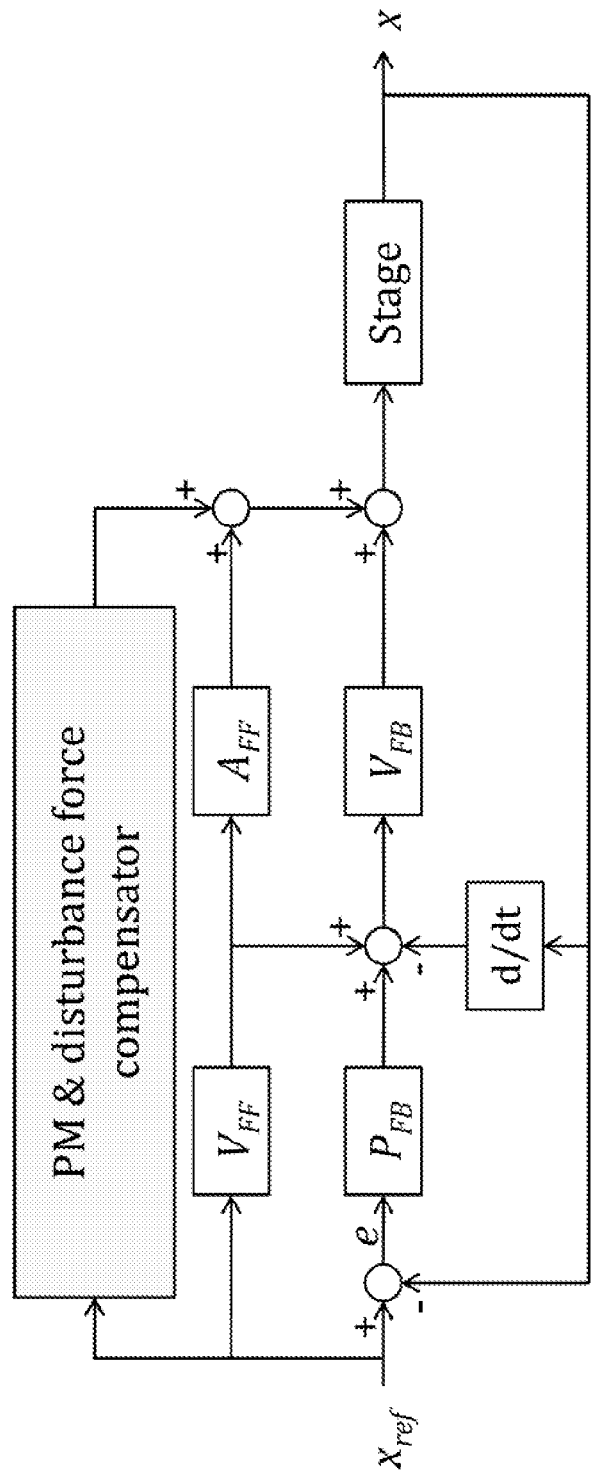
FIG. 5 illustrates a control scheme of the magnet assisted stage system, with P, V, and A denoting position, velocity, and acceleration, respectively.

In some embodiments, a cascaded P/PI feedback (FB) controller with velocity and acceleration feed forward (FF) is used to control the position of scanning table 18. It can be implemented using a real time controller running at 10 kHz sampling frequency to achieve a closed loop bandwidth of about 290 Hz. Additional feed forward permanent magnet force and disturbance compensators are implemented to reject known disturbances as illustrated in the block diagram of FIG. 5. The role of the permanent magnet force compensator is to cancel the spill-over assistive forces in the constant velocity region of each scan, based on the measured $F_{PM}(d)$ curve of the permanent magnets. The disturbance force compensator cancels out the position and velocity dependent disturbance force ripples associated with the linear motor.

EXPERIMENTAL RESULTS

Figure 6A:
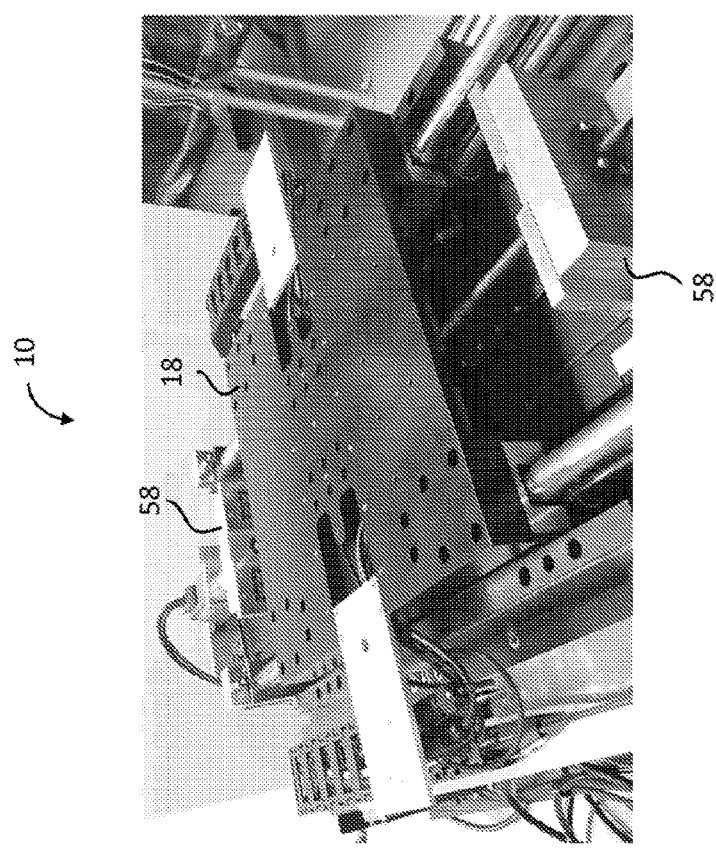
FIG. 6A is a photograph of the magnet assisted stage system.
Figure 6B:
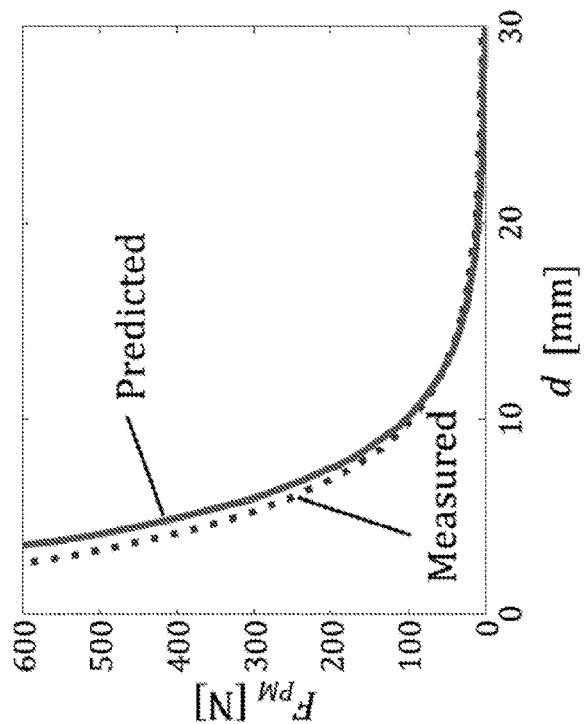
FIG. 6B is a graph illustrating the predicted and measured $F_{PM}(d)$ curves of each passive assist device.

FIG. 6A illustrates an in-house-built prototype of magnet assisted stage system 10 as described herein. The predicted and experimentally measured $F_{PM}(d)$ curves of each passive assist device are illustrated in FIG. 6B. They are in good agreement and confirm that the stage is capable of providing the needed maximum assistive force (525 N) at a gap of 3.2 mm between the magnets while providing less than 4 N of assistive force at a gap of 30 mm.

Figure 7A:
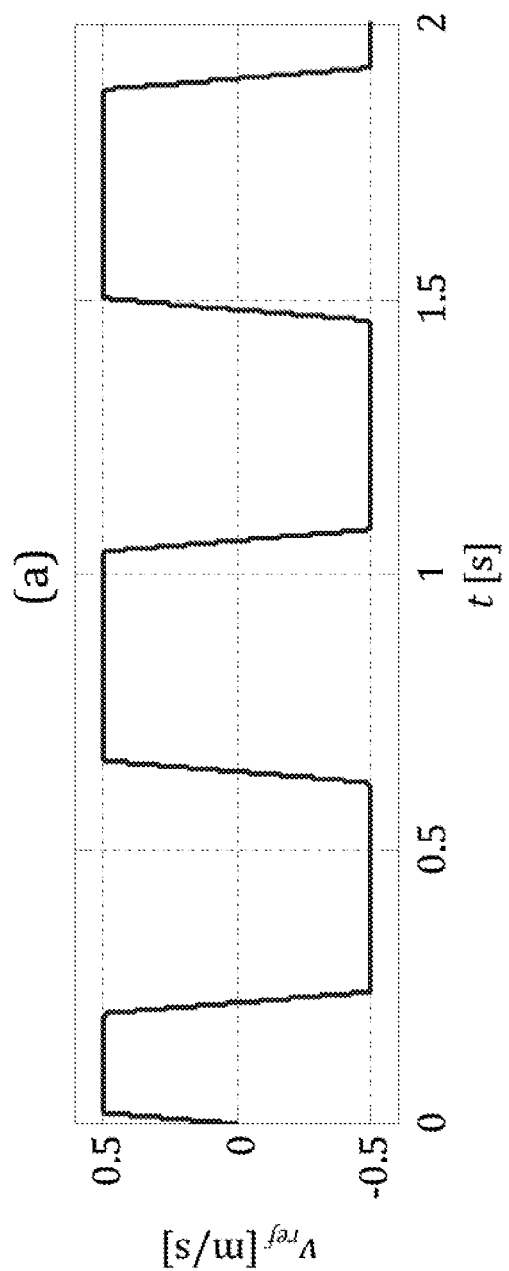
FIG. 7A is a graph illustrating reference trajectory used in experiments for a reference velocity trajectory for 0.5 m/s scan speed.

The trapezoidal acceleration scan trajectory whose velocity profile is illustrated in FIG. 7A is used to demonstrate the performance of the stage. The parameters of the trajectory are summarized in Table 2. The minimum distance between the permanent magnets of the passive assist device is determined as 3.3 mm based on minimizing heat using the method discussed herein.

TABLE 2

Parameters used in reference trajectory generation

| Parameter | Value |
| --- | --- |
| Max. jerk | 500 m/s³ |
| Max. acceleration | 25 m/s² (2.5 g) |
| Scan speed | 0.5 m/s |
| Scan stroke | 200 mm |
| $d_{min}$ | 3.3 mm |

Figure 7B:
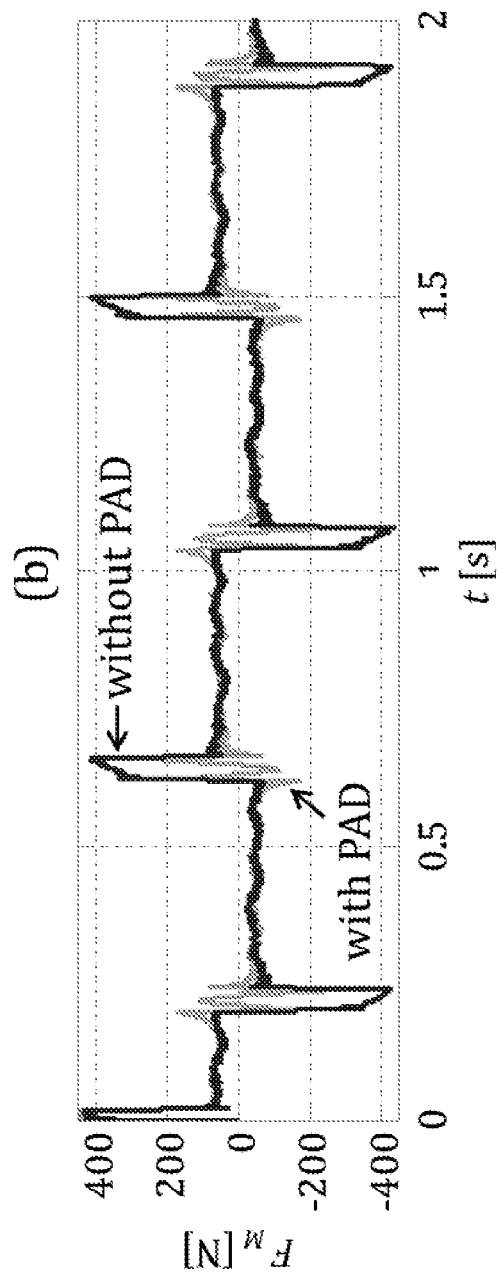
FIG. 7B is a graph illustrating the measured system response for a linear motor force applied to a moving table.
Figure 7C:
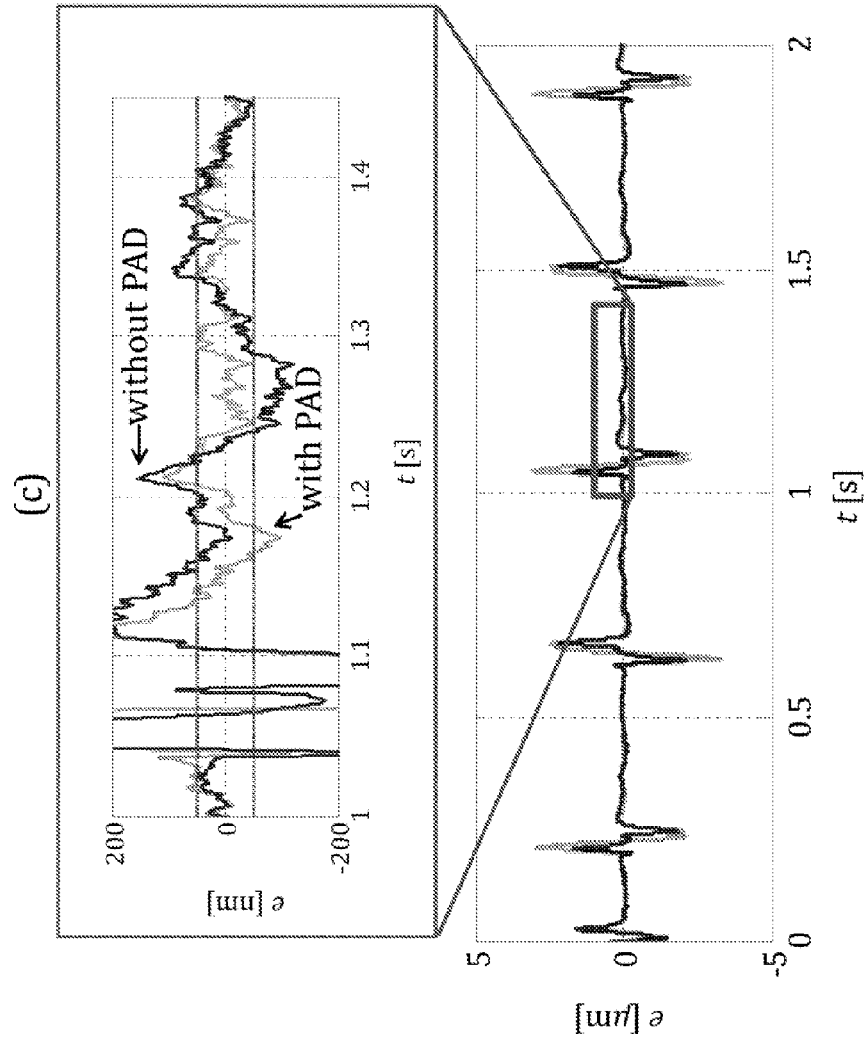
FIG. 7C is a graph illustrating the measured system response for position error.
Figure 7D:
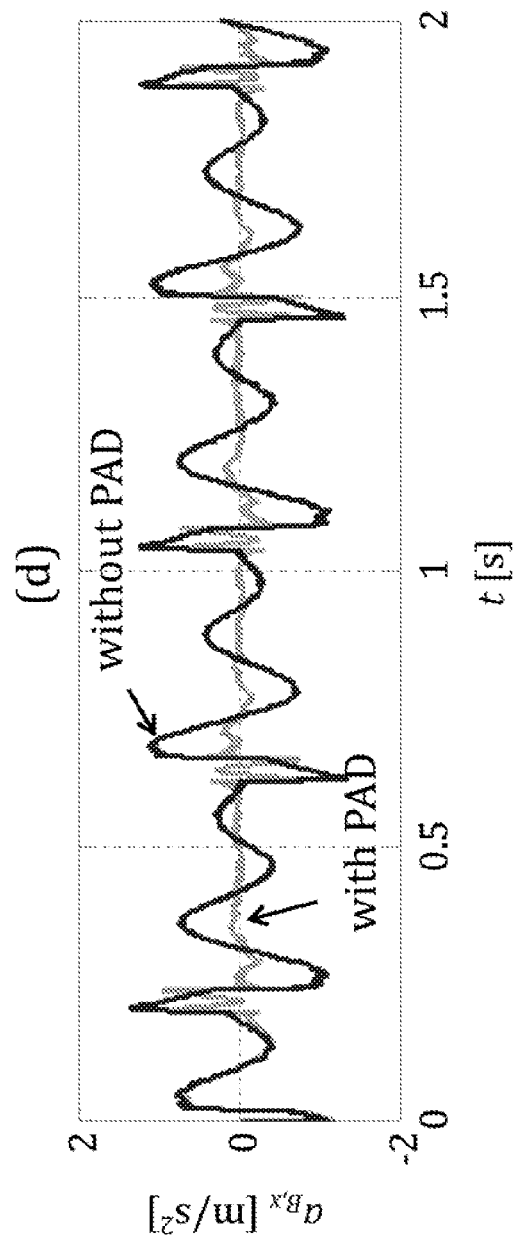
FIG. 7D is a graph illustrating the measured system response for horizontal (x-axis) vibration of the isolated base.

FIGS. 7B, 7C, and 7D, respectively, show the measured motor force $F_M$, position tracking error, and residual vibration of the isolated base 14 in the horizontal direction (x-axis). High frequency contents of the position error signal have been filtered using a 10 ms-window moving average filter, as is customary in wafer scanning applications. When there is no passive assist device, $F_M$ equals 123 $N_{RMS}$. However, when using magnet assisted stage system 10 located at the calculated optimal location, $F_M$ drops to 63 $N_{RMS}$ (i.e., 49% reduction). Consequently, using $K_M=15.13$ NW$^{-0.5}$, the Joule heating of the linear motors is calculated from Eq. (1) to decrease from 48.4 J to 21.8 J (i.e., 55% reduction), per scan period, with the help of the proposed passive assist devices. By the same token, the RMS value of $a_{B,x}$, the residual vibration of the base in the x-direction, drops from 0.492 m/s² to 0.169 m/s² (i.e., 66% reduction). This leads to a 55% decrease in settling time from 290 ms to 130 ms, using a 50 nm position error window.

CONCLUSIONS

Accordingly, magnet assisted stage system 10 has been shown to reduce motor heat and residual vibration for scanning applications. Assistive forces are applied to the scanning table during motion reversal (MR) regions using a pair of repelling permanent magnets (PMs) at each end of the stage. The assistive forces provided by the PMs are channeled to the ground, rather than to the vibration-sensitive machine base, thus reducing residual vibration and enhancing scanning speed. The position of the PMs relative to each other is designed to be adjustable so that they can be configured to minimize heat or vibration. Using PMs to provide assistive forces has the added advantage of reducing the ground vibration transmitted to the scanning table during high precision constant velocity scanning, because of the nonlinear force-distance curve of PMs. Experiments conducted on a prototype stage constructed based on the present invention demonstrate excellent results with regard to both vibration and heat reduction.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically illustrated or described. The same may also be varied in many ways. Such variations are not to be regarded as a departure from the disclosure, and all such modifications are intended to be included within the scope of the disclosure.

What is claimed is:

1. A magnet assisted stage system for scanning applications, said system comprising:
   a scanning table being moveable from a first position to a second position;
   a scanning actuator operably associated with said scanning table to move said scanning table along a scanning direction from said first position to said second position; and
   an actively variable magnetic spring system being operably augmented to said scanning table, said actively variable magnetic spring system exerting a magnetic force upon said scanning table in said scanning direction;
   wherein said actively variable magnetic spring system comprises a permanent magnet exerting a repulsive force upon said scanning table, a gap between said permanent magnet and said scanning table being actively varied to vary an effective spring stiffness acting on said scanning table.

2. The magnet assisted stage system according to claim 1 wherein said actively variable magnetic spring system is moveable relative to a ground.

3. The magnet assisted stage system according to claim 2, further comprising a linear actuator configured to move said actively variable magnetic spring system relative to said ground.

4. The magnet assisted stage system according to claim 2 wherein said actively variable magnetic spring system is operable to isolate vibration and heat transfer from transmission to said scanning table.

5. A magnet assisted stage system for scanning applications, said system comprising:
   a scanning table being moveable from a first position to a second position;
   a scanning actuator operably associated with said scanning table to move said scanning table along a scanning direction from said first position to said second position; and
   an actively variable magnetic spring system being operably augmented to said scanning table, said actively variable magnetic spring system exerting a magnetic force upon said scanning table in said scanning direction,
   wherein said actively variable magnetic spring system comprises a pair of permanent magnets on opposing sides of said scanning table, a first of said pair of permanent magnets being mounted upon said side of said scanning table and a second of said pair of permanent magnets being mounted upon a ground, a gap between said first and said second permanent magnets being varied to vary an effective spring stiffness acting on said scanning table.

6. The magnet assisted stage system according to claim 5 wherein said second permanent magnet is moveable relative to said ground.

7. A magnet assisted stage system for scanning applications, said system comprising:
   a scanning table being moveable from a first position to a second position;
   a scanning actuator operably associated with said scanning table to move said scanning table along a scanning direction from said first position to said second position;
   an actively variable magnetic spring system being operably augmented to said scanning table, said actively variable magnetic spring system exerting a magnetic force upon said scanning table in said scanning direction; and
   a stepping actuator operably associated with said scanning table to move said scanning table along a stepping direction, said stepping direction being orthogonal to said scanning direction,
   wherein said actively variable magnetic spring system further exerts a magnetic force upon said scanning table in said stepping direction.

8. A magnet assisted stage system for scanning applications, said system comprising:
   a base;
   a scanning table being moveable from a first position to a second position to support a wafer;
   a scanning actuator operably associated with said scanning table to move said scanning table along a scanning direction from said first position to said second position; and
   an actively variable magnetic spring system being operably associated with said scanning table, said actively variable magnetic spring system having a permanent magnet coupled with said base and exerting a repulsive magnetic force upon said scanning table in said scanning direction, a gap between said permanent magnet and said scanning table being actively varied to vary an effective spring stiffness acting on said scanning table.

9. The magnet assisted stage system according to claim 8 wherein said actively variable magnetic spring system is moveable relative to said base.

10. The magnet assisted stage system according to claim 9, further comprising a linear actuator configured to move said actively variable magnetic spring system relative to said base.

11. The magnet assisted stage system according to claim 8 wherein said actively variable magnetic spring system is operable to isolate vibration and heat transfer from transmission to said scanning table.

12. The magnet assisted stage system according to claim 8 wherein said actively variable magnetic spring system comprises a pair of permanent magnets on opposing sides of said scanning table, a first of said pair of permanent magnets being mounted upon said side of said scanning table and a second of said pair of permanent magnets being mounted upon said base, a gap between said first and said second permanent magnets being varied to vary an effective spring stiffness acting on said scanning table.

13. The magnet assisted stage system according to claim 12 wherein said second permanent magnet is moveable relative to said base.

14. The magnet assisted stage system according to claim 8, further comprising:
- a stepping actuator operably associated with said scanning table to move said scanning table along a stepping direction, said stepping direction being orthogonal to said scanning direction,
- wherein said actively variable magnetic spring system further exerts a magnetic force upon said scanning table in said stepping direction.

* * * * *